(12) United States Patent
Nakauchi et al.

(10) Patent No.: US 6,627,792 B2
(45) Date of Patent: Sep. 30, 2003

(54) HUMAN T CELL-ENGRAFTED MOUSE, METHOD FOR DEVELOPING SAME AND USE THEREOF

(75) Inventors: Hiromitsu Nakauchi, 429-3, Ohi, Kukizaki-cho Inashiki-gun, Ibaraki, 300-1243 (JP); Yutaka Fujiki, Tsukuba (JP); Dongku Kim, New York, NY (US)

(73) Assignees: Fujisawa Pharmaceutical Co., Ltd., Osaka (JP); Hiromitsu Nakauchi, Inashiki-gun (JP)

( * ) Notice: Subject to any disclaimer, the term of this patent is extended or adjusted under 35 U.S.C. 154(b) by 0 days.

(21) Appl. No.: 09/429,110

(22) Filed: Oct. 28, 1999

(65) Prior Publication Data

US 2002/0152484 A1 Oct. 17, 2002

(30) Foreign Application Priority Data

Apr. 28, 1999 (JP) ............................................ 11-123183

(51) Int. Cl.[7] ............................................. A01K 67/00
(52) U.S. Cl. ................................ 800/9; 800/8; 800/11; 800/13; 800/14; 800/18
(58) Field of Search .............................. 800/11, 9, 8, 3, 800/14, 18, 21

(56) References Cited

PUBLICATIONS

Kim et al., Eur. J. Haematol., vol. 61, pp. 93–99, 1998.*
Hesselton et al., J. Infect Diseases, vol. 172, pp. 974–782, 1995.*
Heike et al., Blood, vol. 86, pp. 524–530, Jul. 1995.*
Grigoriy Kovalev et al., The Journal of Immunology, 1999, 162: pp. 7555–7562, by *The American Association of Immunologists*, Induction of MHC Class I Expression on Immature Thymocytes in HIV–1–Infected SCID–hu Thy/Liv Mice: Evidence of Indirect Mechanisms[1].

Cheryl A. Stoddart et al., Antimicrobial Agents and Chemotherapy, Aug. 1988, pp. 2113–2115, Inhibition of Human Immunodeficiency Virus Type 1 Infection in SCID–hu Thy/Liv Mice by the G–Quartet–Forming Oligonucleotide, ISIS 5320.

McCune, J.M., et al., "The SCID–hu Mouse: murine Model for the Analysis of Human Hematolymphoid Differentiation and Function", *Science*, vol. 241, pp. 1632–1639 (Sep., 1988).

Mosier D.E., et al., "Transfer of a functional human immune system to mice with severe combined immunodeficiency," *Nature*, vol. 335, pp .256–259 (Sep., 1988).

Kim, D.K., et al. "Engraftment of human myelodysplastic syndrome derived cell line in transgenic severe combined immunodeficient (TG–SCID) mice expressing human GM–CSF and IL–3," *Eur. J. Haematol.*, vol. 61, pp. 93–99 (1998).

Hesselton, R.M., et al., "High Levels of Human Peripheral Blood Mononuclear Cell Engraftment and Enhanced Susceptibility to Human Immunodeficiency Virus Type 1 Infection in NOD/LtSz–scid/scid Mice," *Jour. Of Infect. Disease*, vol. 172 pp. 974–982 (Oct., 1995).

Heike, Yuji, et al., "Long–Term Human Hematopoiesis in SCID–hu Mice Bearing Transplanted Fragments of Adult Bone and Bone Marrow Cells," *Blood*, vol. 86, No. 2, pp. 524–530 (Jul., 1995).

\* cited by examiner

*Primary Examiner*—Michael Wilson
(74) *Attorney, Agent, or Firm*—Oblon, Spivak, McClelland, Maier & Neustadt, P.C.

(57) ABSTRACT

The present invention provides a method for developing a human T cell-engrafted mouse, which includes transplanting a human-derived bone tissue into an inbred line mouse deficient in immune cells, and a human T cell-engrafted mouse obtainable by the method. The present invention also provides a method for preparing an HIV-infected mouse model, which includes infecting the human T cell-engrafted mouse with HIV, and an HIV-infected mouse model obtainable by the method.

8 Claims, 10 Drawing Sheets

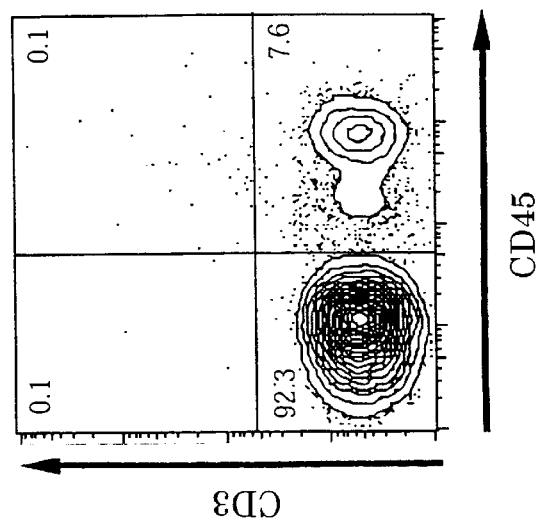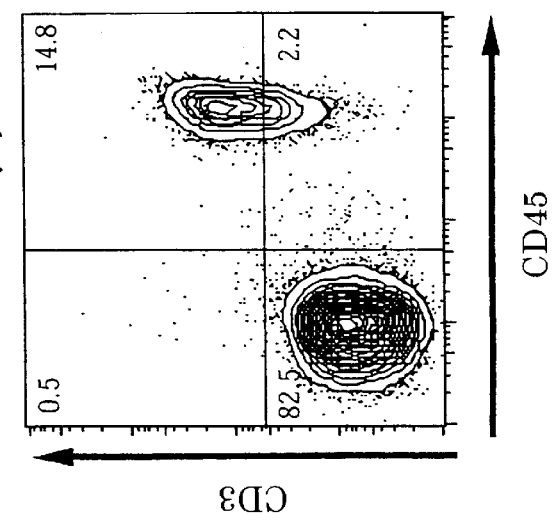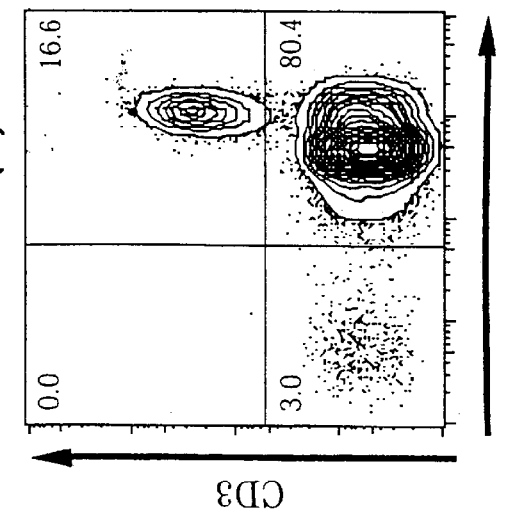

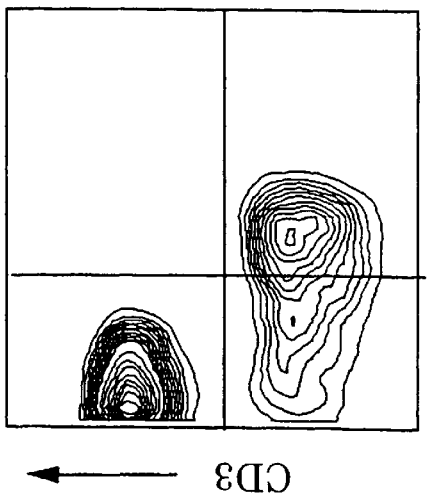
FIG. 3 (C) — 12 weeks after transplantation
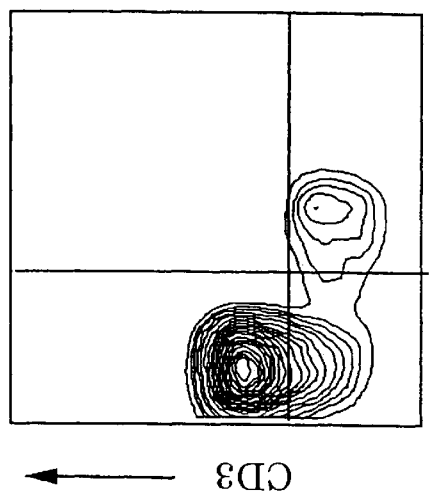
FIG. 3 (B) — 8 weeks after transplantation
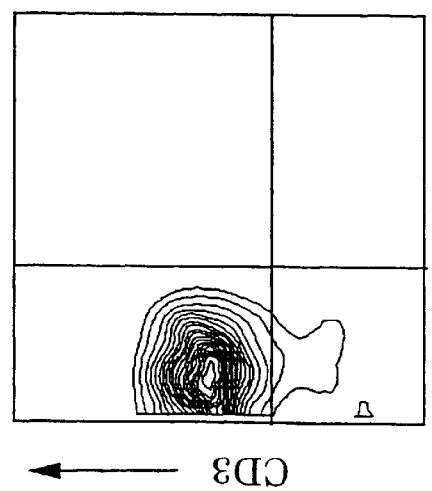
FIG. 3 (A) — 4 weeks after transplantation

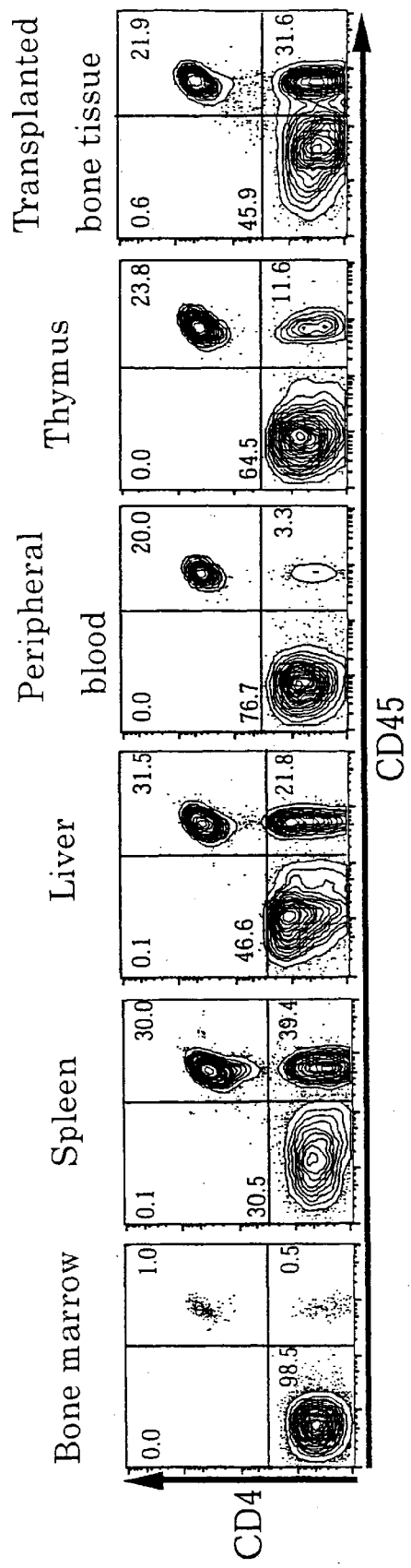
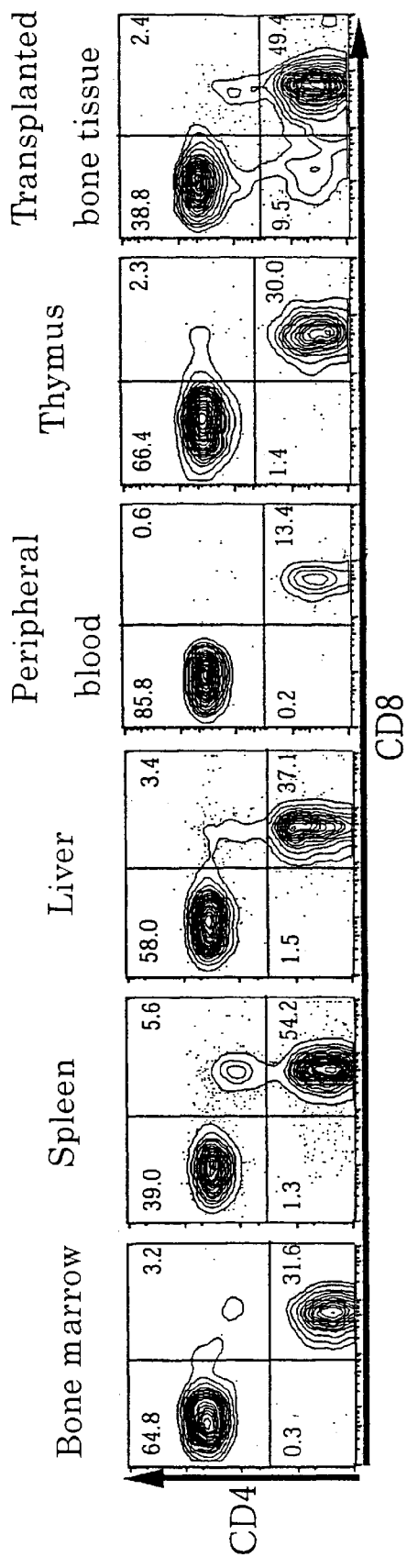
FIG.7(A)
FIG.7(B)

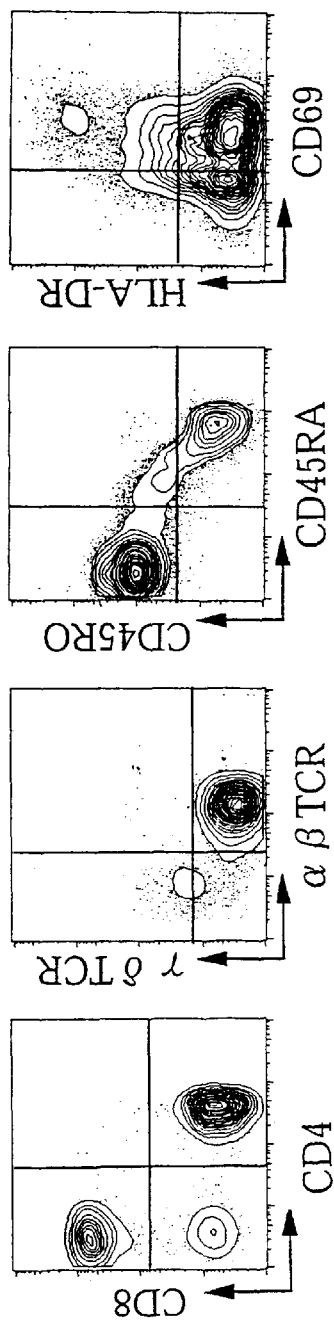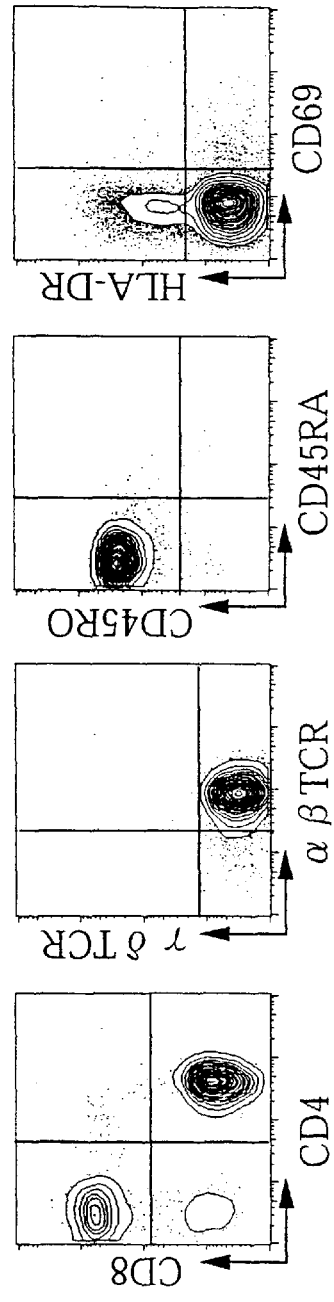

Before infection with HIV 2 weeks after infection with HIV

HUMAN T CELL-ENGRAFTED MOUSE, METHOD FOR DEVELOPING SAME AND USE THEREOF

TECHNICAL FIELD OF THE INVENTION

The present application claims priority under 35 U.S.C. §119 to Japanese Application No. JP 11-123183 filed Apr. 28, 1999.

The present invention relates to a novel mouse, in which human T cells have been engrafted, which is useful as an animal model for the in vivo analysis of the differentiation and proliferation of human T cells, functions thereof and the like, and to a method for developing the mouse. More particularly, the present invention relates to a method for developing a novel human T cell-engrafted mouse, which comprises transplanting a human-derived bone tissue into an inbred line mouse deficient in immune cells such as B cells and T cells, as well as to a novel mouse obtainable by this method, in which human T cells are present in blood at a high percentage for a long period of time. Furthermore, the present invention relates to an application of the novel mouse as an infectious model with a human immunodeficiency virus (hereinafter abbreviated as HIV).

BACKGROUND OF THE INVENTION

In spite of great efforts so far made to overcome AIDS, a conclusive method for treating this infectious disease having a high morbidity and mortality has not been established. One of the serious obstacles in the studies of treatment of AIDS at animal levels is that small animals in wide use, such as mouse, are not infected with HIV. While experiments using primates, such as rhesus monkey, have been recently performed, the primates are highly expensive and cannot be used frequently for laboratory level experiments. Therefore, there is a great demand for developing a mouse model artificially treated to become susceptible to HIV infection.

A primary approach to solving the above-mentioned problem is to make HIV infectious human-derived immune cells exist within the body of a mouse. Thus, many attempts have been made to develop a mouse model having human blood cells, in particular, human T cells, by transplanting a tissue comprising these cells or a tissue capable of producing them into a mouse.

For example, J. M. McCune et al. (Science, 241(4873): 1632–1639 (1988)) transplanted fetal human tissues (thymus and liver or bone) to under renal epithelium of a C.B.-17 scid/scid mouse (hereinafter to be referred to as SCID mouse), which congenitally lacks mature B and T cells due to gene rearrangement function disorder, whereby a SCID-hu mouse was prepared, in which hemopoietic stem cells derived from the liver or bone marrow appear in the periphery via the transplanted human thymus, so that human T cells are identified in the peripheral blood. In most cases, however, the frequency of appearance of human cells in this mouse is very low. Moreover, a fetal human tissue is not readily available. Accordingly, this mouse is not predominantly used.

In contrast, an hu-PBL-SCID mouse (D. E. Mosier et al., Nature, 335(6187): 256–259 (1988)), which is prepared by intraperitoneally administering nucleated cells in human peripheral blood or peripheral blood stimulated with IL-2 to a SCID mouse, in which human T cells appear in peripheral blood, is being used in number at present as an experimental model for HIV infection, because it can be produced overwhelmingly easily as compared to the SCID-hu mouse. However, this mouse again shows low frequency of human T cell appearance. In addition, this mouse disadvantageously shows an unusual $CD4^+$ cell/$CD8^+$ cell ratio (hereinafter to be abbreviated as CD4/CD8 ratio) wherein CD8 positive cells are mostly dominant.

In view of the low proportion of human T cells in peripheral blood of any mouse model, T cell chimerism in blood has been improved by irradiation or administration of an anti-NK antibody (D. K. Kim et al., Eur. J. Haematol., 61(2): 93–99 (1998)).

A NOD/Shi-scid Jic (NOD/SCID) mouse, which has been recently developed (R. M. Hesselton et al., J. Infect. Dis., 172(4): 974–982 (1995)), shows lower activities of not only T cell and B cell but also other immune cells such as NK cell and macrophage, thereby allowing 5 to 10 times higher incidence of engrafting of human cells than in conventional SCID mice. Even if this mouse is used as a recipient for an hu-PBL-SCID, however, the T cells of the resulting mouse are still CD8 positive cell-dominant, which means that the mouse is insufficient as a model for HIV infection.

While there are some reports on transplantation of a bone tissue derived from a human adult into a SCID mouse (e.g., Y. Heike et al., Blood, 86(2): 524–530 (1995)), none of which succeeded in engrafting human T cells.

As mentioned above, all conventional human T cell-engrafted mice have a drawback, such as a low frequency of appearance of human T cells in blood, a failure to sustain the effect for a long time and/or a different CD4/CD8 ratio from a human, i.e., being CD8 positive cell dominant and the like. As the situation stands, there has not been found any satisfactory HIV infection model.

SUMMARY OF THE INVENTION

It is therefore an object of the present invention to provide a human T cell-engrafted mouse in which human T cells appear in blood at a high frequency for a long time and which has a CD4/CD8 ratio approximate to that of human, and a method for developing such mouse. It is a further object of the present invention to provide an HIV-infected mouse model superior to conventional ones, by infecting a human T cell-engrafted mouse model with HIV.

The present inventors have transplanted a bone tissue derived from a human adult to an inbred line mouse lacking immune cells including B cells and T cells, particularly NOD/SCID mouse, as a recipient. As a result, they have succeeded in providing a mouse, in which T cells can proliferate and which shows high T cell chimerism in blood for a long time. In addition, they have confirmed that the mouse shows significantly higher CD4/CD8 ratios in blood and each organ than those of known mouse models, and is more preferable as an HIV infection model. Furthermore, the present inventors actually infected this mouse with HIV and confirmed reduction of CD4 positive T cells after infection, demonstrating that the mouse model can be a superior HIV infection model, which resulted in the completion of the present invention.

Accordingly, the present invention provides the following.

(1) A human T cell-engrafted mouse, wherein human bone tissue-derived T cells exist in peripheral blood at least for 2 months, and, for a certain period of time during this 2 month period, a proportion of human cells in blood becomes more than 10%, preferably more than 30%.

(2) A method for developing a human T cell-engrafted mouse comprising transplanting a human-derived bone tissue into an inbred line mouse lacking immune cells inclusive of at least B cells and T cells, preferably an inbred line mouse further deficient in NK cell activity and/or macrophage activity, most preferably a NOD/SCID mouse, preferably into the extraperitoneal cavity of said recipient.

(3) The human T cell-engrafted mouse obtainable by the method of (2) above, wherein human bone tissue-derived T cells exist in peripheral blood at least for 2 months from about 1 month to about 3 months after transplantation, and, for a certain period of time during this 2 month period, a proportion of human cells in blood becomes more than 10%, preferably more than 30%.

(4) The mouse of (1) or (3) above, wherein a part of said human T cells is capable of being infected with HIV.

(5) A method for preparing an experimental HIV-infected mouse model, which comprises infecting the mouse of (4) above with HIV.

(6) An experimental HIV-infected mouse model obtainable by the method of (5) above.

According to the method of the present invention, it is possible to develop a blood-chimeric mouse in which human T cells appear in peripheral blood at a high frequency for a long time, and the inventive method is useful in in vivo analysis of differentiation/proliferation and functions of human T cells. This mouse model also serves well as a recipient of immune response induced by transplantation of tumor cells. Furthermore, since the blood-chimeric mouse prepared by the inventive method has a higher CD4/CD8 ratio than that of conventional mice, and has T cells that express both CD4 and CXCR4 markers, which are HIV receptors, it is strikingly useful as a model of HIV infection.

BRIEF DESCRIPTION OF THE DRAWINGS

FIGS. 2(A), 2(B) and 2(C) show proportions of human and non-human T cells in peripheral blood cells of mice transplanted with a human bone tissue (FIG. 2(B)) or human bone marrow cell (FIG. 2(C)), wherein the figure at the upper part of each quadrant shows the proportion (%) thereof to the total cells. FIG. 2(A) is a control (human peripheral blood).

FIGS. 3(A), 3(B) and 3(C) show changes in the frequency of appearance of human T cells and human B cells in peripheral blood of mice transplanted with a human bone tissue (only CD45 positive cells were gated in).

FIGS. 7(A) and 7(B) show frequencies of appearance of human cells in the bone marrow, spleen, liver, peripheral blood, thymus and transplanted human bone tissue of a mouse transplanted with the human bone tissue (FIG. 7(A)), and proportions of CD4 positive and CD8 positive cells in the human cells (FIG. 7(B)), wherein the figure at the upper part of each quadrant shows the proportion (%) thereof to the total cells.

FIGS. 8(A) and 8(B) show phenotypes of T cells in human peripheral blood (FIG. 8(A)) and human T cells appearing in peripheral blood of a mouse transplanted with a human bone tissue (FIG. 8(B)) (only CD3 positive cells were gated in).

FIG. 9(B) shows that a part of human T cells appearing in peripheral blood of a mouse transplanted with a human bone tissue is CD4 and CXCR4 double positive. The cells in the area pointed with an arrow are infected with HIV. FIG. 9(A) is a control (human peripheral blood). In both cases, only CD3 positive cells were gated in.

DETAILED DESCRIPTION OF THE INVENTION

Figure 1:
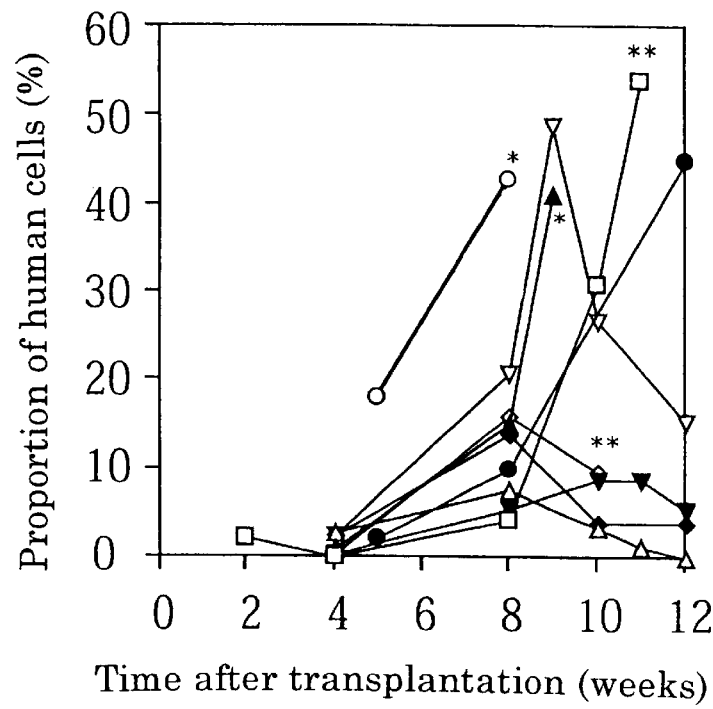
FIGS. 1(A) and 1(B) show changes in the proportion of human cells in peripheral blood cells of mice transplanted with a human bone tissue (FIG. 1(A)) or human bone marrow cell (FIG. 1(B)), wherein * means death of mouse during the test and ** means sacrifice of mouse for other analysis.
Figure 1:
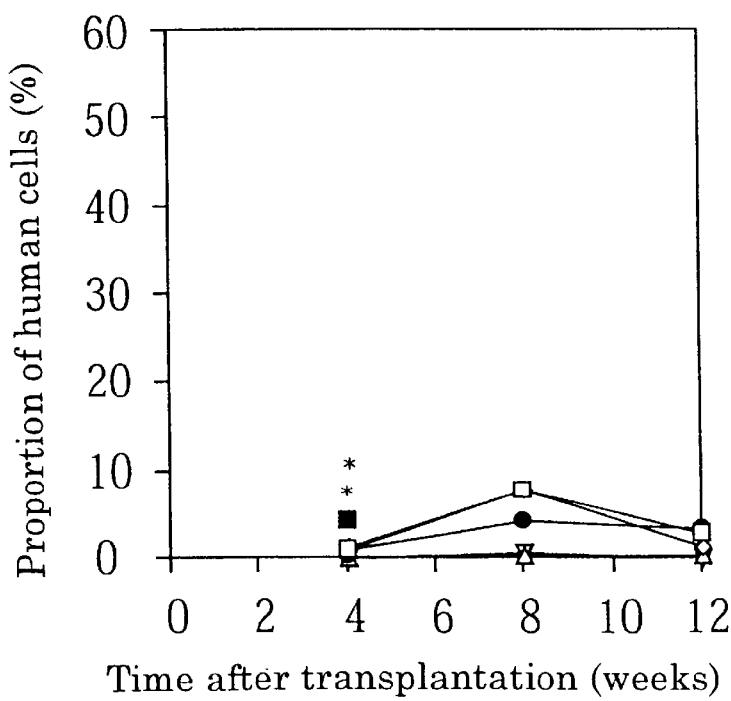

The mouse of the present invention may be prepared by any method, as long as human bone tissue-derived T cells exist in peripheral blood of the mouse for at least 2 months, and, for a certain period of time during this 2 month period, the proportion of the human cells in blood exceeds 10%. Its origin is not particularly limited. It is, however, preferable that the inventive mouse be made by transplanting a human-derived bone tissue into an inbred line mouse lacking immune cells including at least B cells and T cells, preferably an inbred line mouse further deficient in NK cell activity and/or macrophage activity. An inbred line mice lacking B cells and T cells includes, for example, SCID mouse and the like. An inbred line mice further deficient in activities of other immune cells, such as NK cells and macrophages, may be a NOD/SCID mouse. In such human T cell-engrafted mouse developed by transplanting a human-derived bone tissue into a mouse congenitally deficient in immune cells, human T cells begin to appear in peripheral blood about 4 weeks after transplantation, and, for a certain period of time thereafter, the proportion of human cells in blood cells exceeds 10%. Preferably, in such mouse, the proportion of human cells in blood cells exceeds 30%, at maximum beyond 50% in some cases. Such high proportion of human cells lasts for at least about 3 months after transplantation.

In a particularly preferable embodiment of the present invention, a NOD/SCID mouse is used as a recipient. While sex, age and the like of the recipient mouse are not limited, for example, an 8 to 12-week-old mouse can be used. The mouse used may be bred under conventional conditions, but an SPF-mouse is preferably employed.

While the human bone tissue to be transplanted into the mouse of the present invention is not particularly limited by its site, the condition of donor and the like, as long as it comprises bone marrow cells, it is preferably a human bone tissue other than fetal one, more preferably a bone tissue derived from a human adult, for example, a bone tissue derived from a rib of a human adult and the like. When free bone marrow cells are used, however, appearance thereof in blood is less frequent and the appearance lasts only for a short time, though T cells get engrafted. Hence, the bone tissue to be transplanted preferably comprises stroma cells such that the steric structure of bone marrow is maintained and human microenvironment can be reproduced in the body of a mouse.

For example, a bone is excised in an operation and immediately, or after storage at a low temperature of 0–4° C.

until use, aseptically cut into pieces of about 6–8 mm in size to expose bone marrow tissue. The number of bone marrow cells in the bone tissue graft to be transplanted are about $10^{6-10^9}$, preferably about $10^{7-10^8}$, most preferably about $2-5\times10^7$.

Prior to transplantation of the bone tissue, the recipient mouse may be irradiated or an anti-NK antibody may be administered thereto on demand to lower the function of an autoimmune system of the mouse, but transplantation without a pre-treatment is also preferable. When irradiation is performed, for example, a sub-lethal dose (about 3.0–3.2 Gy) is irradiated.

While the human bone tissue can be transplanted into any site of the recipient mouse, as long as the transplantation can result in the engraftment of human T cells in the mouse, it is preferably transplanted subcutaneously into the extraperitoneal cavity. In this case, the bone tissue is preferably transplanted by making the exposed bone marrow surface closely adhered to the peritoneum.

After transplantation, the mouse may be bred under the same conditions as before. The appearance of human T cells in peripheral blood can be monitored by sampling blood every 2–4 weeks after transplantation and analyzing same by, for example, flow cytometry. For example, hematocytes in peripheral blood sampled from fundus venous plexus, tail vein or the like are hemolyzed to concentrate leukocytes, which are double stained with an anti-human CD45 antibody and antibodies against various differentiation antigens (e.g., CD3, CD 13, CD 19, CD33, CD34, CD56 and the like), and analyzed with a fluorescence activated cell sorter (FACS). Inasmuch as T cells are CD3 positive, human T cells are detected as CD45 positive/CD3 positive.

In another embodiment, human B cells are further engrafted in the mouse of the present invention in addition to T cells. The engraftment of B cells more frequently appears in a mouse without irradiation prior to transplantation. The engraftment of B cells tends to be 2 weeks later than the engraftment of T cells. Inasmuch as B cells are CD 19 positive, they can be detected as CD45 positive/CD 19 positive in the above-mentioned flow cytometry.

In the inventive mouse, human T cells appear in not only peripheral blood but also various organs. The chimerism of human T cells varies depending on organs. Human T cells mostly appear in the liver and spleen, but otherwise in the bone marrow. The distribution thereof in peripheral blood and thymus is in between the distributions in the liver and the spleen.

The mouse of the present invention is characterized by a higher CD4/CD8 ratio as compared to that in known human T cell-engrafted mice. This tendency is more noticeable in peripheral blood than in other organs. CD4 positive T cells are helper cells supporting the functions of other T cells and B cells, which express CD45RO out of CD45 shared leukocyte antigens, or helper/inducer cells inducing killer T cells and the like, which express CD45RA out of CD45 shared leukocyte antigens. The former corresponds to sensitized memory cells and the latter corresponds to immature T cells. On the other hand, CD8 positive T cells are cytotoxic (killer) T cells.

The human T cells appearing in peripheral blood of the inventive mouse are T cells expressing αβT cell receptor (αβTCR), which occupy not less than 90% of human peripheral blood T cells, and are of CD45RO positive mature memory cell type. Only a part of the human T cells expresses activation markers, and therefore, the human T cells have not been activated strongly.

The human T cells appearing in peripheral blood of the inventive mouse are polyclonal and in the form of a chimera of cells expressing various types of Vβ marker antigens.

The human T cells appearing in peripheral blood of the inventive mouse are further characterized by the expression of, CXCR4, a co-receptor for HIV infection, in partial CD4 positive cells. Consequently, the inventive mouse can be preferably used as an HIV infection model.

An HIV-infected mouse model can be prepared by administering HIV, in an amount sufficient for infection, for example, intravenously, intraarterially, intramuscularly, intradermally, intraperitoneally, and the like, into the mouse of the present invention. Of the human T cells, CD4 positive cells are specifically infected with HIV. Therefore, the viral infection can be confirmed by monitoring the reduction in the CD4/CD8 ratio.

The mouse of the present invention can be preferably used not only as an HIV infection model but also as, for example, a model for analyzing development and differentiation of T cells and a recipient of tumor cell transplantation to investigate effects of tumor immune.

The present invention is described in more detail by referring to following Examples and Experimental Examples. These are mere exemplification and do not limit the scope of the present invention.

EXAMPLE A

Transplantation of Human Bone Tissue into Mouse

A NOD/Shi-scid Jic mice (purchased from Clea Japan, Inc.) were bred in Animal Experiment Center, University of Tsukuba, and animals in 8–12 weeks of age were used as recipients. A rib excised from an adult patient suffering from lung cancer during the operation carried out in Thoracic Surgery, University of Tsukuba, was obtained with informed consent of the patient, and stored at 4° C. for several hours before transplantation. The rib was aseptically cut into sections having a size of 6–8 mm (approximately $2-5\times10^7$ bone marrow cells) to expose bone marrow tissue. The bone tissue sections were subcutaneously transplanted into the extraperitoneal cavity of NOD/SCID mice exposed to a sub-lethal dose (300 cGy), in such a manner that the exposed bone marrow surface was closely adhered to the peritoneum. For transplantation, the mice were anesthetized by intraperitoneal injection of Nembutal.

Comparitive Example 1

Transplantation of Bone Marrow Cell Suspension into Mouse

Bone marrow cells (approximately $2\times10^7$ cells), which were prepared in the form of a cell suspension by removing the bone from the rib section obtained in Example 1, were transplanted into NOD/SCID mice by an injection into the tail vein.

Experimental Example 1

Change in Chimerism of Peripheral Blood of the Bone Tissue- or Bone Marrow Cell-Transplanted Mouse Peripheral blood of each human bone tissue-transplanted mouse obtained in Example 1 was sampled from fundus venous plexus under anesthesia from 2 weeks after transplantation, at various intervals of 1 to 4 weeks. Hematocytes were lysed with ammonium chloride. The resulting concentrated leukocytes were stained with an anti-CD45 antibody and antibodies against various differentiation antigens (CD3, CD 13, CD 19, CD33, CD34 and CD56), and analyzed with a cell sorter (FACS Vantage; manufactured by Becton Dickinson). The leukocytes were mixed with the above antibodies and washed twice with medium for staining. PI was further added to gate out dead cells. FACS analysis was performed in 3 or 4 colors. At least 30,000 leukocytes were analyzed. As a result, human cells (CD45 positive cells) were not detected in peripheral blood at 2 weeks after transplantation and began to appear from 4 weeks after transplantation. The frequency of appearance increased at 8 weeks after transplantation. In a certain mouse, more than 50% of blood cells became human-derived at 10 weeks after transplantation. The human cells continued to appear in peripheral blood thereafter and were detected until at least 12 weeks after transplantation (FIG. 1(A)). Most of the engrafted cells were T cells, the average proportion of CD3 positive cells (i.e., T cells) in CD45 positive cells at 8 weeks after transplantation was 69.5±17.5% (n=9) (FIG. 2(B)). In contrast, the peripheral blood of the mouse transplanted with a bone marrow cell suspension, obtained in Comparative Example 1, also became chimeric with human cells, but human cell chimerism was low (FIG. 1(B)) and T cells were hardly observed (FIG. 2(C)).

Experimental Example 2

Engraftment of B Cells in Human Bone Tissue-Transplanted Mouse

The leukocytes, which were sampled from the mice obtained in Example 1 and treated in the same manner as in Experimental Example 1, were stained with an anti-CD 19 antibody and an anti-CD3 antibody, and analyzed with FACS. As a result, the engraftment of not only T cells but B cells was observed in some mice. The engraftment of B cells was observed in 3% of the irradiated recipient mice and 42% of the non-irradiated mice. Furthermore, the engraftment of B cells had a tendency of being detected about 2 weeks after the engraftment of T cells (FIG. 3). On the other hand, human myeloids, erythroids and NK cells were not identified in any mice except one.

Experimental Example 3

Appearance and Pathological Observation of Human Bone Tissue-Transplanted Mouse

Figure 4:
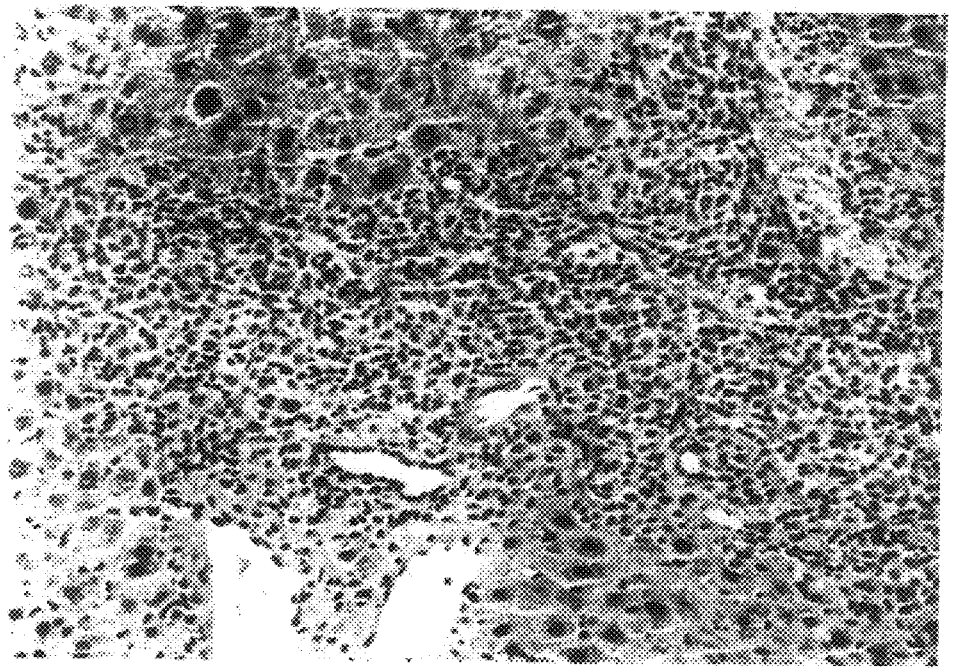
FIGS. 4(A) and 4(B) are photographs of hematoxylin-eosin staining of the livers of a mouse transplanted with a human bone tissue (FIG. 4(A)) and a naive recipient mouse (FIG. 4(B)).
Figure 4:
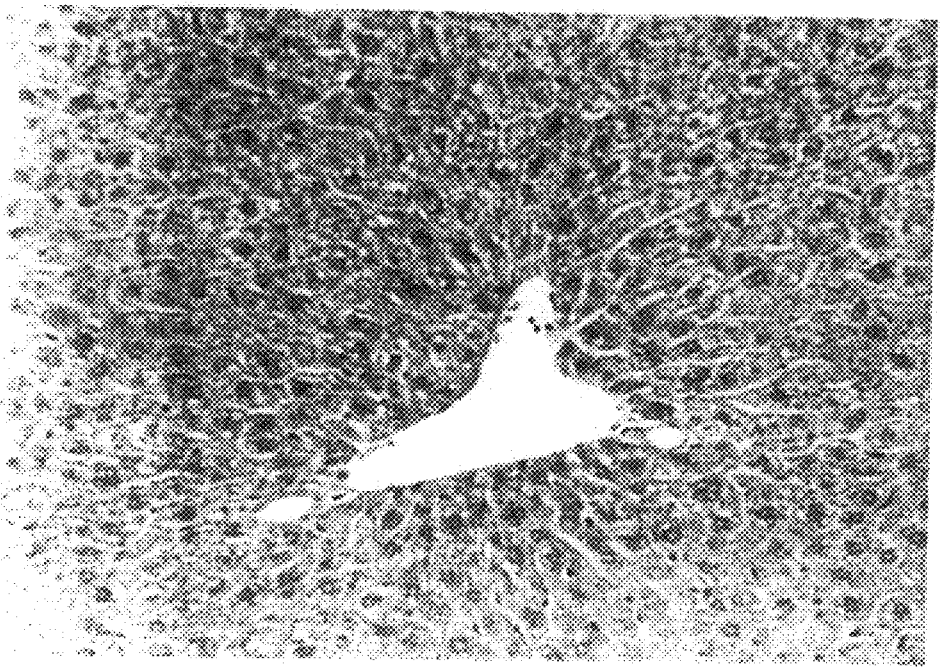
Figure 5:
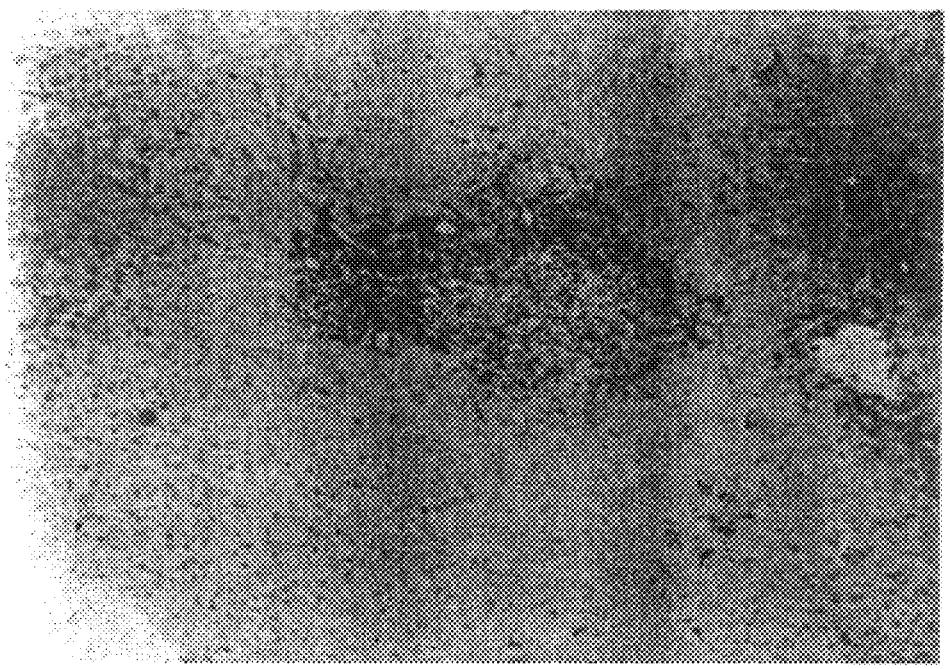
FIGS. 5(A) and 5(B) are photographs of immunostaining of the livers of a mouse transplanted with a human bone tissue (FIG. 5(A)) and a naive recipient mouse (FIG. 5(B)).
Figure 5:
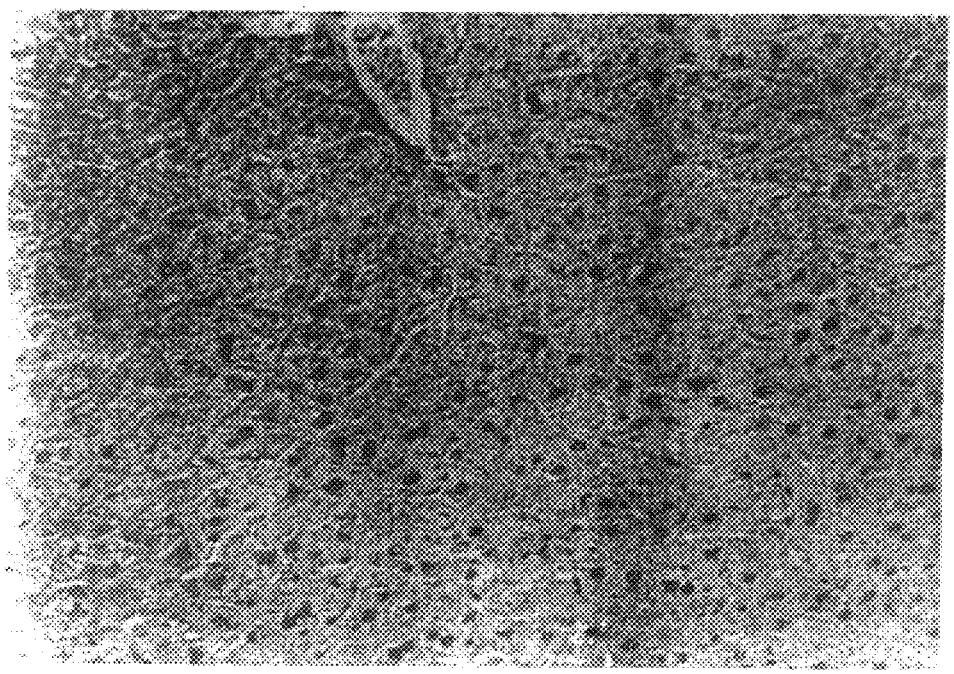
Figure 6:
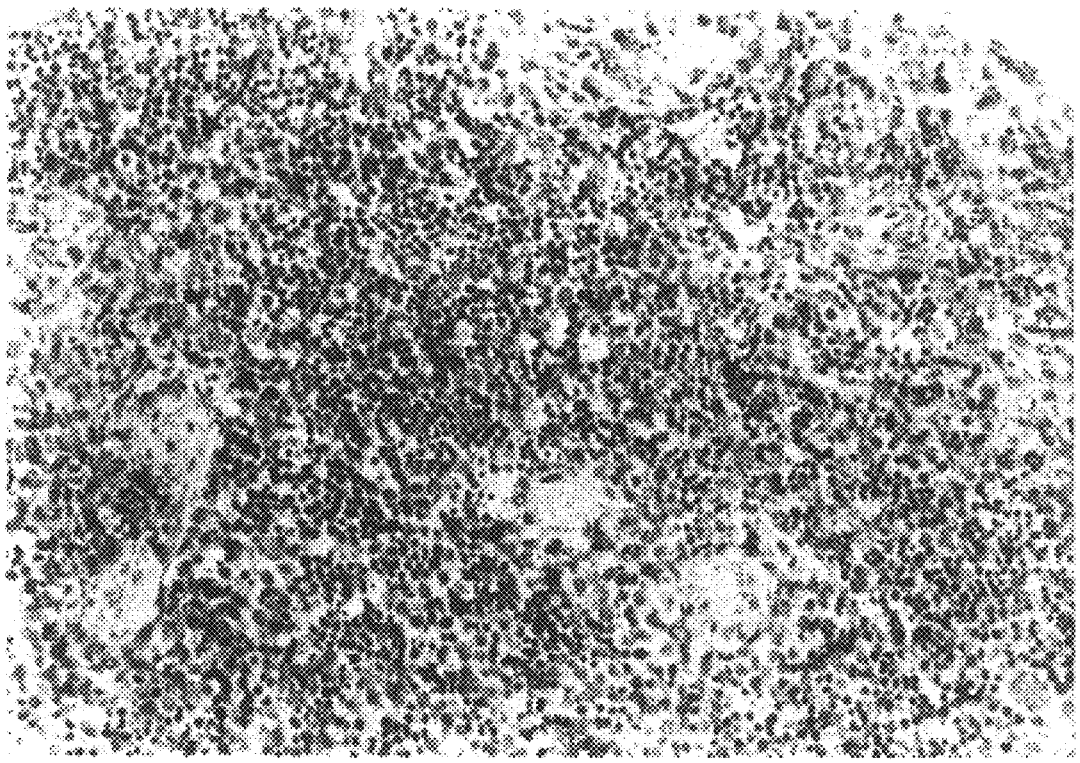
FIG. 6 is a photograph of immunostaining of the spleen of a mouse transplanted with a human bone tissue.

The human bone tissue-transplanted mice obtained in Example 1 grew well, and no symptoms like graft versus host disease (GVHD), such as diarrhea and weight loss, were observed. At 8 weeks after transplantation, the bone marrow part of the transplanted human bone tissue was replaced with an adipose tissue. The thymus could not be identified or was very small when it existed. No hypertrophy, swelling or reddening of the spleen or liver was observed. The mouse that showed chimerism of about 20% in peripheral blood was euthanized, the liver and spleen were excised and fixed with formalin. The liver was stained with hematoxylin-eosin. The liver and spleen were subjected to immunostaining using an enzyme-labeled anti-CD3 antibody. As a result, the border between human lymphocytes and normal tissue was relatively clear in the liver, and atypical lymphocytes existed as if they formed a colony (FIG. 4(A) and FIG. 5(A)). The immunohistological staining of the spleen revealed human lymphocytes seemingly existed diffusely (FIG. 6). In kidney, acute tubular necrosis was not observed. Although an infiltration of human lymphocytes was observed, the infiltration looked different from that found in GVH reaction.

Experimental Example 4

Chimerisms in Various Organs

Some of the mice obtained in Example 1 were euthanized, the bone marrow, spleen, liver, thymus and transplanted bone tissue were excised and blood cells were separated from each of them to give concentrated leukocytes. The leukocytes were stained with an anti-CD45 antibody and an anti-CD4 antibody, and analyzed with FACS. As a result, human lymphocytes were rich in the liver and spleen, while poor in bone marrow, and in between the two in peripheral blood (FIG. 7(A)). The sorted CD45 positive cells were further analyzed with FACS using an anti-CD4 antibody and an anti-CD8 antibody. As a result, most of the human T cells were single positive, i.e., CD4 positive or CD8 positive cells, but a part of them was double positive, i.e., CD4 positive and CD8 positive T cells (FIG. 7(B)), which suggests that human T cells has been differentiated in the organs of mice.

Experimental Example 5

Phenotypes of Human T Cells in Mouse Peripheral Blood

To further clarify the characteristics of the engrafted human T cells, human cells were stained with various antibodies. The concentrated leukocytes prepared in the same manner as in Experimental Example 1 were stained with an anti-CD4 antibody and an anti-CD8 antibody, an anti-αβTCR antibody and an anti-γδTCR antibody, an anti-CD45RA antibody and an anti-CD45RO antibody or an anti-CD69 antibody and an anti-HLA-DR antibody, and analyzed with FACS. As a result, these T cells comprised αβTCR and were CD45RA negative/RO positive. The results suggest that these cells are mature memory cell type T cells. Only a part of these cells expressed activation markers, CD69 and HLA-DR (FIG. 8(B)).

Experimental Example 6

Confirmation of the Clonality of Human T Cells

To confirm the clonality of the engrafted human T cells, FACS analysis and RT-PCR were performed. In FACS analysis, the human T cells were stained with an anti-Vβ3TCR antibody, an anti-Vβ5.2TCR antibody or an anti-Vβ8.1 and 8.2 antibody in combination with an anti-CD45 antibody and an anti-CD3 antibody (Table 1). Separately, cDNA was reverse-transcribed from peripheral blood RNA, and subjected to RT-PCR using 23 kinds of Vβ specific primers (Table 2). As is evident from the Tables, human T cells were confirmed to be polyclonal.

TABLE 1

| | percentage of Vβ+/CD3+cells (%) | | |
|---|---|---|---|
| | Vβ3 | Vβ5.2 | Vβ8.1 & 8.2 |
| Human A | 2.91 | 0.33 | 3.90 |
| Human B | 4.55 | 0.47 | 2.98 |
| Mouse 1 | 2.73 | 0.46 | 4.16 |

TABLE 1-continued

| | percentage of Vβ+/CD3+cells (%) | | |
|---|---|---|---|
| | Vβ3 | Vβ5.2 | Vβ8.1 & 8.2 |
| Mouse 2 | 2.43 | 3.67 | 1.29 |
| Mouse 3 | 0.08 | 0.08 | 3.41 |
| Mouse 4 | 2.98 | 0.47 | 0.57 |

TABLE 2

| | human | mouse No. | | | |
|---|---|---|---|---|---|
| VβTCR | control | 1 | 2 | 3 | 4 |
| 1 | + | + | + | + | + |
| 2 | + | + | + | + | − |
| 3 | + | + | + | + | + |
| 4 | + | + | + | + | − |
| 5.1 | + | + | + | + | + |
| 5.2 | + | + | − | + | + |
| 6 | + | + | + | + | + |
| 7 | + | + | − | + | + |
| 8 | + | + | + | + | + |
| 9 | + | + | − | + | + |
| 10 | + | + | + | + | + |
| 11 | + | − | − | − | − |
| 12 | + | + | + | + | + |
| 13.1 | + | + | + | + | + |
| 13.2 | + | + | + | + | − |
| 14 | + | + | + | + | + |
| 15 | + | N.D. | N.D. | N.D. | N.D. |
| 16 | + | + | − | + | + |
| 17 | + | + | + | + | + |
| 18 | + | + | + | + | + |
| 19 | + | + | + | + | + |
| 20 | + | + | − | + | − |
| 21 | + | + | − | + | + |

Experimental Example 7

Expression of HIV Receptor on Human T Cells in Mouse Peripheral Blood

Figure 9:
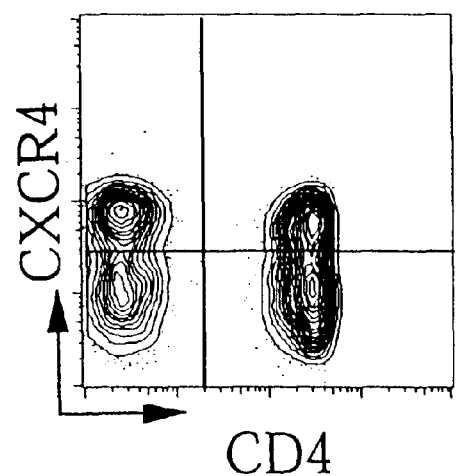
Figure 9:
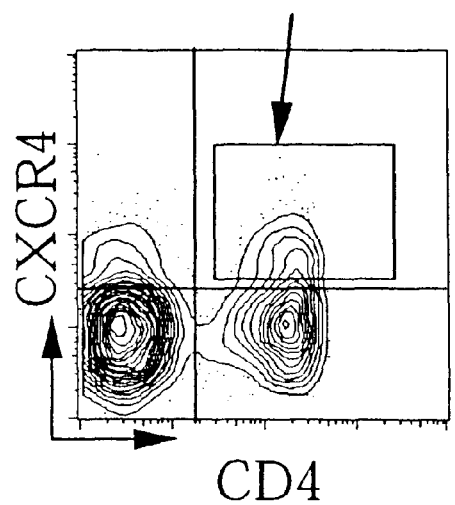

To study whether the human T cell-engrafted mouse can be used as an HIV infection model, expression of an HIV co-receptor, CXCR4, on CD4 positive cells was confirmed with FACS (FIG. 9). As a result, it was confirmed that CD4/CXCR4 double positive T cells existed, though the frequency of appearance thereof was lower than that of human peripheral blood.

EXAMPLE B

Preparation of HIV Infection Model

Figure 10:
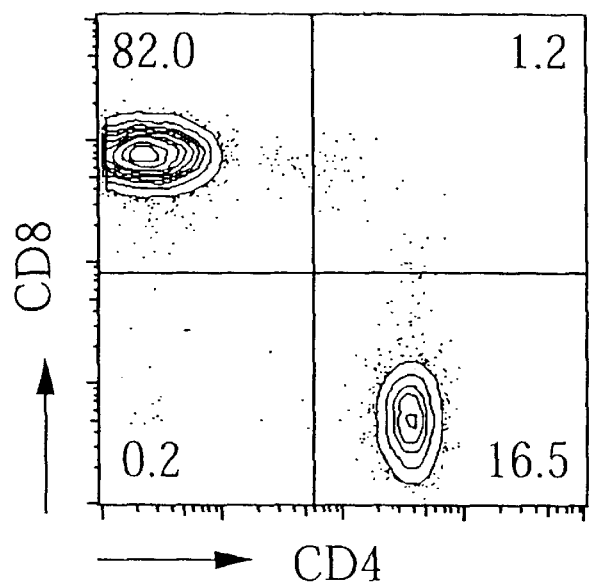
FIGS. 10(A) and 10(B) show reduction of CD4 positive cells appearing in peripheral blood of a mouse transplanted with a human bone tissue, from before the infection (FIG. 10(A)) to after infection (FIG. 10(B)) with HIV, wherein the figure at the upper part of each quadrant shows the proportion (%) thereof to the total cells. Determination was performed by gating in only the CD3 positive cells.
Figure 10:
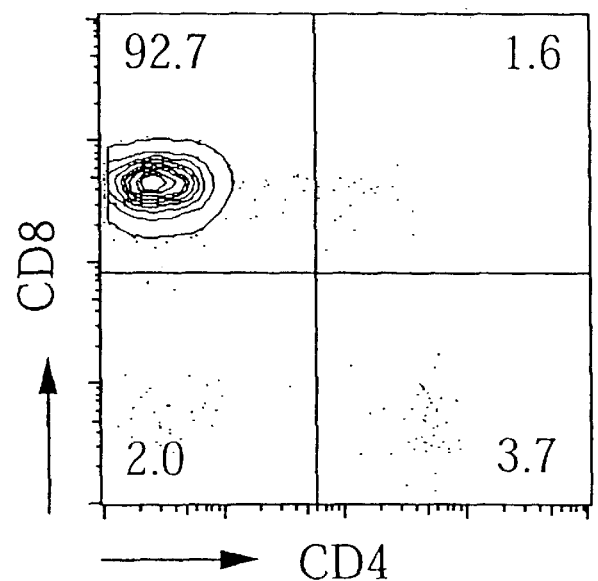

A mouse (7 weeks after transplantation of bone tissue, human T cell chimerism in peripheral blood 8.3%) was infected with HIV by an intravenous injection. Two weeks later, the blood was sampled and subjected to FACS analysis to investigate changes in CD4/CD8 ratio (FIG. 10). As a result, the chimerism reduced to 5.5% and CD4/CD8 ratio changed from 20.1% to 4.0%, which confirmed a significant decrease in CD4 positive cells. Viral antigen p24 was detectable in serum by ELISA, which revealed that this infected mouse had viremia.

This application is based on application No. 123183/1999 filed in Japan, the content of which is incorporated hereinto by reference. All publications are herein incorporated by reference to the same extent as if each individual publication was specifically described herein.

What is claimed is:

1. A NOD/SCID mouse comprising human CD45 positive peripheral blood lymphocytes, which appear in the peripheral blood of the mouse for at least two months, wherein during part of the at least two months, the human CD45 positive peripheral blood lymphocytes are present in a proportion of at least 10% of the total peripheral blood lymphocytes in the mouse, and wherein the mouse is prepared by transplanting a fragment of human bone subcutaneously into the extra-peritoneum of said NOD/SCID mouse.

2. The mouse of claim 1, wherein during part of the at least two months the human CD45 positive peripheral blood lymphocytes are present in the amount of at least 30% of the total peripheral blood lymphocytes.

3. The mouse of claim 1, wherein during part of the at least two months the human CD45 positive peripheral blood lymphocytes are present in the amount of at least 50% of the total peripheral blood lymphocytes.

4. The mouse of claim 1, wherein said human CD45 positive peripheral blood lymphocytes are polyclonal.

5. A method of infecting the mouse of claim 1 with human immunodeficiency virus (HIV) comprising introducing said HIV into the mouse; and measuring the level of CD4-positive human T cells and CD8-positive human T cells, wherein a reduction in the ratio of CD4-positive human T cells to CD8-positive human T cells compared to said mouse prior to introducing said HIV indicates HIV infection.

6. The method of claim 5, wherein during a part of the at least two months the human CD45 positive peripheral blood lymphocytes are present in the amount of at least 30% of the total peripheral blood lymphocytes in the mouse.

7. The method of claim 5, wherein during a part of the at least two months the human CD45 positive peripheral blood lymphocytes are present in the amount of at least 50% of the total peripheral blood lymphocytes.

8. The method of claim 5, wherein said human CD45 positive peripheral blood lymphocytes are polyclonal.

* * * * *